United States Patent
James et al.

(10) Patent No.: US 10,166,320 B2
(45) Date of Patent: Jan. 1, 2019

(54) DETECTING A HEATER BAG

(71) Applicant: Fresenius Medical Care Holdings, Inc., Waltham, MA (US)

(72) Inventors: Philip Scott James, Orinda, CA (US); Kulwinder S. Plahey, Martinez, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 476 days.

(21) Appl. No.: 14/851,280

(22) Filed: Sep. 11, 2015

(65) Prior Publication Data
US 2017/0072124 A1 Mar. 16, 2017

(51) Int. Cl.
*A61M 1/28* (2006.01)
*A61M 1/16* (2006.01)

(52) U.S. Cl.
CPC ............ *A61M 1/282* (2014.02); *A61M 1/166* (2014.02); *A61M 1/28* (2013.01); *A61M 1/287* (2013.01); *A61M 2205/14* (2013.01); *A61M 2205/3327* (2013.01); *A61M 2205/3368* (2013.01); *A61M 2205/3372* (2013.01); *A61M 2205/36* (2013.01); *A61M 2205/3653* (2013.01); *A61M 2205/50* (2013.01); *A61M 2205/6018* (2013.01)

(58) Field of Classification Search
CPC .. A61M 1/282; A61M 2205/14; A61M 1/284; A61M 1/287; A61M 1/28; A61M 1/166; A61M 1/1664; A61M 5/44; A61M 5/445
See application file for complete search history.

(56) References Cited

U.S. PATENT DOCUMENTS

| | | |
|---|---|---|
| 7,207,966 B2 | 4/2007 | Savare et al. |
| 7,789,850 B2 | 9/2010 | Roger |
| 9,585,992 B2 | 3/2017 | Bene |
| 2002/0032403 A1 | 3/2002 | Savagle et al. |
| 2008/0058712 A1 | 3/2008 | Plahey |
| 2008/0177222 A1 | 7/2008 | Roger |
| 2009/0009179 A1 | 1/2009 | Sobue et al. |
| 2009/0299273 A1 | 12/2009 | Lee et al. |

(Continued)

FOREIGN PATENT DOCUMENTS

| | | |
|---|---|---|
| DE | 102012006149 A1 | 3/2012 |
| WO | WO2008106452 A1 | 9/2008 |
| WO | WO2009148987 A2 | 12/2009 |

OTHER PUBLICATIONS

Notification of Transmittal of the International Search Report and the Written Opinion of the International Searching Authority for corresponding PCT Application No. PCT/US2016/048306, dated Nov. 14, 2016, 12 pages.

(Continued)

*Primary Examiner* — Nathan R Price
*Assistant Examiner* — Courtney Fredrickson
(74) *Attorney, Agent, or Firm* — Fish & Richardson P.C.

(57) ABSTRACT

In one aspect, a peritoneal dialysis (PD) machine can be used to detect a heater bag filled with dialysate. The PD machine has a heater tray that includes a temperature sensor and also has a processor that determines a status of the heater bag based on data received from the temperature sensor. For example, the status may be presence of the heater bag on the heater tray and/or correct positioning of the heater bag on the heater tray.

17 Claims, 10 Drawing Sheets

(56) References Cited

U.S. PATENT DOCUMENTS

| | | | |
|---|---|---|---|
| 2011/0315611 A1* | 12/2011 | Fulkerson | A61M 1/3639 |
| | | | 210/96.2 |
| 2013/0006171 A1* | 1/2013 | Griessmann | A61M 1/166 |
| | | | 604/29 |
| 2014/0199057 A1 | 7/2014 | Hansen et al. | |
| 2015/0129499 A1 | 5/2015 | Bene | |
| 2015/0144543 A1* | 5/2015 | Kondo | G01F 1/684 |
| | | | 210/137 |

OTHER PUBLICATIONS

Honeywell, Force Sensors Line Guide 2017, 5 pages.
Honeywell, Sensors in Hemodialysis Machines, An Application Note 2016, 6 pages.
Vecchi et al., "Experimental Evaluation of Two Commercial Force Sensors for Applications in Biomechanics and Motor Control", $5^{th}$ Ann Conf of Int FES Jun. 2000.
International Preliminary Report on Patentability in International Application No. PCT/US2016/048306, dated Mar. 13, 2018, 8 pages.

* cited by examiner

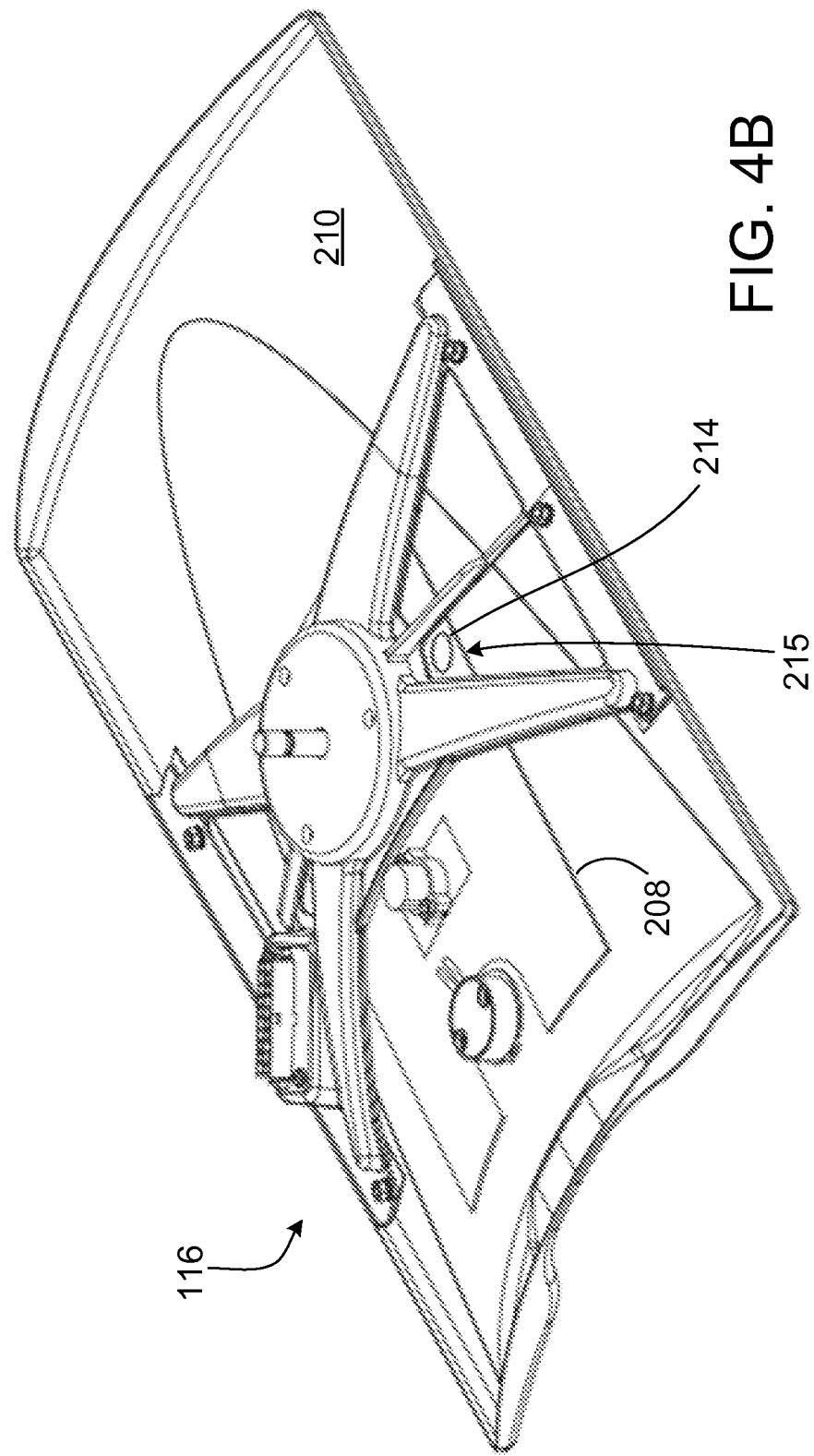

DETECTING A HEATER BAG

TECHNICAL FIELD

This invention relates to dialysis machines, and more particularly to detecting a heater bag being heated by the dialysis machine.

BACKGROUND

Dialysis is a treatment used to support a patient with insufficient renal function. The two principal dialysis methods are hemodialysis and peritoneal dialysis. During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), the patient's peritoneal cavity is periodically infused with dialysate. The membranous lining of the patient's peritoneum acts as a natural semi-permeable membrane that allows diffusion and osmosis exchanges to take place between the solution and the blood stream. These exchanges across the patient's peritoneum result in the removal of waste products, including solutes like urea and creatinine, from the blood, and regulate the levels of other substances, such as sodium and water, in the blood.

Automated PD machines called PD cyclers are designed to control the entire PD process so that it can be performed at home usually overnight without clinical staff in attendance. This process is termed continuous cycler-assisted PD (CCPD). Many PD cyclers are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

The cyclers are designed to manage a number of bags each typically containing up to 5 liters of dialysate. The dialysate is then pumped by the machine or, in so-called gravity systems, allowed by the machine to flow through a patient line to the patient. But, to avoid thermal shock, the dialysate is heated first to near the patient's body temperature before infusion.

One technique for heating the dialysate is to place a dedicated heater bag on top of a heater tray, equipped with heating coils and a temperature sensor. In this arrangement all fluid going to the patient comes from the heater bag. During a dwell period, the heater bag can be refilled from one of several heater bags connected to the machine and warmed so that it will be ready to supply the next fill to the patient.

SUMMARY

In one aspect, a peritoneal dialysis (PD) machine can be used to detect a heater bag filled with dialysate. The PD machine has a heater tray that includes a temperature sensor and also has a processor that determines a status of the heater bag based on data received from the temperature sensor. For example, the status may be presence of the heater bag on the heater tray and/or correct positioning of the heater bag on the heater tray.

Further, in another aspect, a PD machine can detect a heater bag by receiving data from a temperature sensor, comparing temperature values to one or more look-up tables, and determining a status of the heater bag based on the comparison. A computer readable storage device may contain instructions that can be executed by a control unit of the PD machine to carry out these steps as computer system operations.

Implementations and specifics of these techniques are described in detail below. Further, the techniques in this description have a number of advantages. For example, a PD machine can alert a user (e.g., a patient, nurse, technician, etc.) that a heater bag is incorrectly positioned. In response, the user can reposition the bag so that it heats correctly. In addition, this technique can be carried out using temperature sensors, and need not use other kind of sensors such as a weight scale.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A-4E are views of a heater tray.

DETAILED DESCRIPTION

A dialysis machine such as a peritoneal dialysis (PD) machine can be configured to detect whether a heater bag containing dialysate is present and is being heated correctly. A PD machine typically includes a heater tray on which the dialysate heater bag is placed to warm up the dialysate in the bag. If the tray contains heat sensors such as thermistors, a component of the dialysis machine can measure the output of the heat sensors over time to determine if the heater bag is present on the tray and if the heater bag is correctly positioned on the tray. For example, if the output of the heat sensors indicates that the tray is heating up too quickly, then the bag may not be absorbing heat from the tray correctly or the bag may not be present to absorb any heat at all. In response, the dialysis machine could display a message to a user indicating that the bag is positioned incorrectly or is absent.

Figure 1:
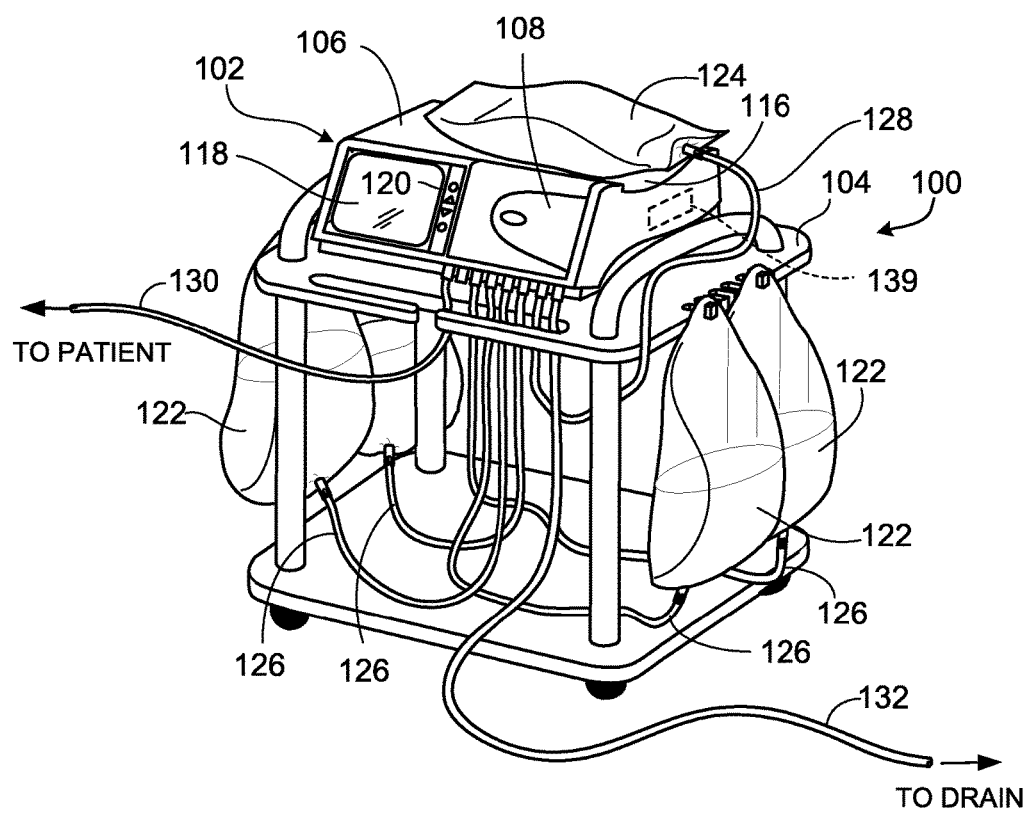
FIGS. 1-2 show a peritoneal dialysis machine.
Figure 2:
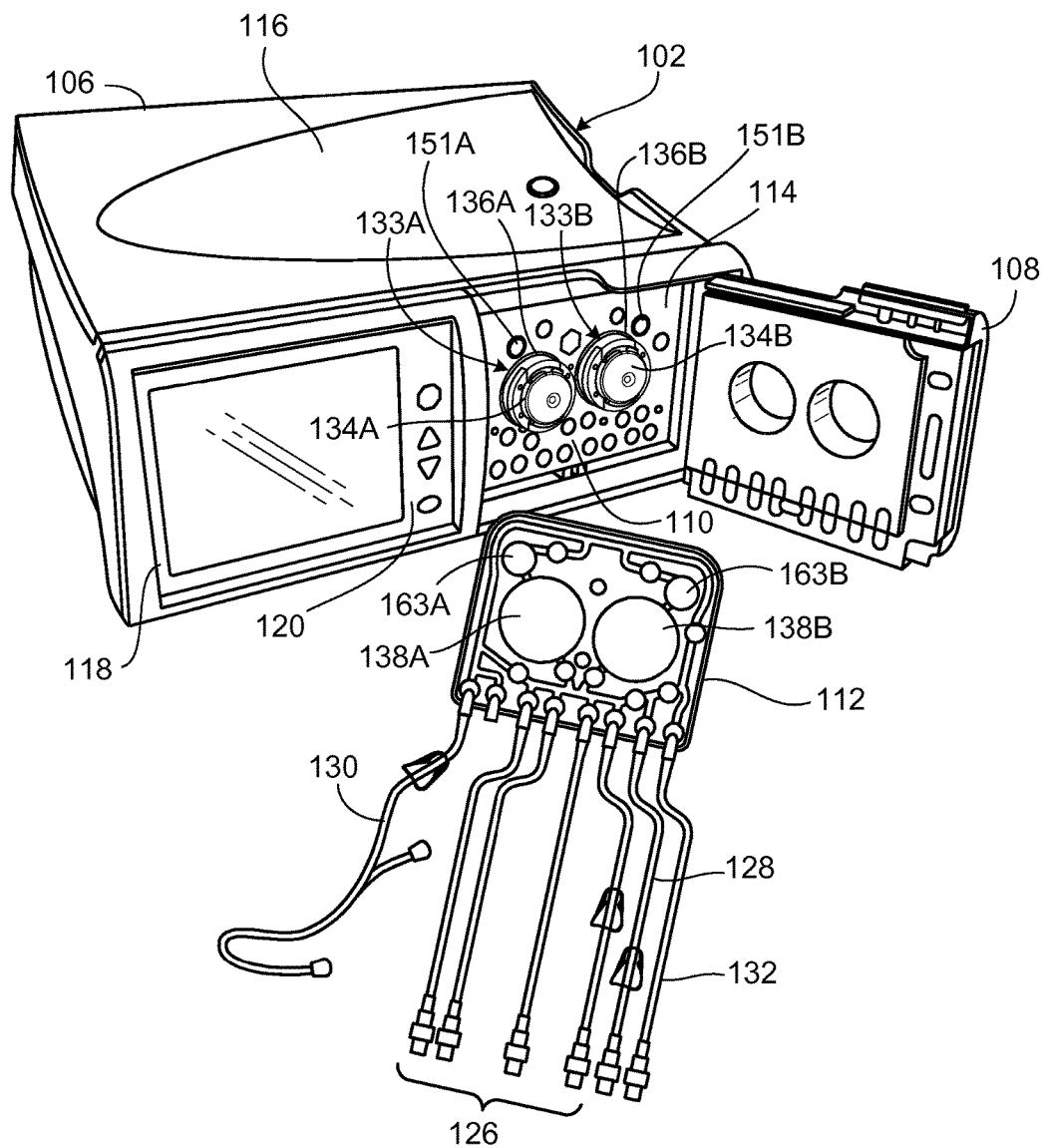

Referring to FIG. 1, a peritoneal dialysis ("PD") system 100 includes a PD cycler (also referred to as a PD machine) 102 seated on a cart 104. Referring also to FIG. 2, the PD cycler 102 includes a housing 106, a door 108, and a cassette interface 110 that contacts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysate (e.g., a 5 liter bag of dialysate). The PD cycler 102 also includes a touch screen 118 and additional control buttons 120 that can be operated by a user (e.g., a patient) to allow, for example, set-up, initiation, and/or termination of a PD treatment.

Dialysate bags 122 are suspended from fingers on the sides of the cart 104, and a heater bag 124 is positioned in the heater tray 116. The dialysate bags 122 and the heater bag 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The drain line 132 can be connected to a drain or drain receptacle and can be used to pass dialysate from the cassette 112 to the drain or drain receptacle during use.

Figure 3:
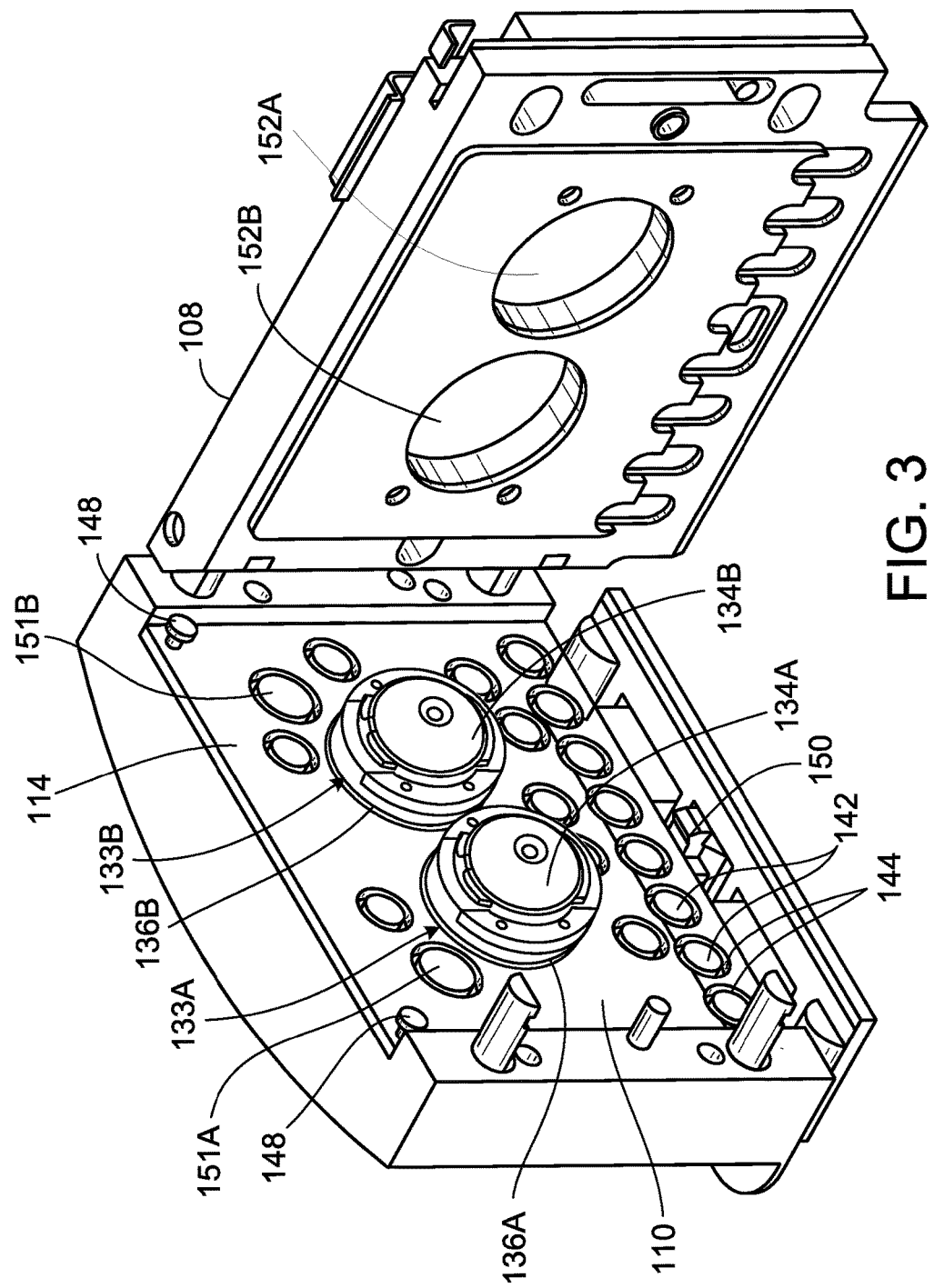
FIG. 3 shows a cassette interface.

FIG. 3 shows a more detailed view of the cassette interface 110 and the door 108 of the PD cycler 102. As shown, the PD cycler 102 includes pistons 133A, 133B with piston heads 134A, 134B attached to piston shafts 135A, 135B (piston shaft 135A shown in FIG. 4) that can be axially moved within piston access ports 136A, 136B formed in the cassette interface 110. The piston shafts 135A, 135B are connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward along the lead screws. The nuts, in turn, are connected to the pistons 133A, 133B and thus cause the pistons 133A, 133B to move inward and outward as the stepper motors rotate the lead screws. Stepper motor controllers provide the necessary current to be driven through the windings of the stepper motors to move the pistons 133A, 133B. The polarity of the current determines whether the pistons 133A, 133B are advanced or retracted. In some implementations, the stepper motors require 200 steps to make a full rotation, and this corresponds to 0.048 inch of linear travel.

The PD system 100 also includes encoders (e.g., optical encoders) that measure the rotational movement of the lead screws. The axial positions of the pistons 133A, 133B can be determined based on the rotational movement of the lead screws, as determined by the encoders. Thus, the measurements of the encoders can be used to accurately position the piston heads 134A, 134B of the pistons 133A, 133B.

When the cassette 112 (shown in FIG. 2) is positioned within the cassette compartment 114 of the PD cycler 102 with the door 108 closed, the piston heads 134A, 134B of the PD cycler 102 align with pump chambers 138A, 138B of the cassette 112 such that the piston heads 134A, 134B can be mechanically connected to dome-shaped fastening members 161A, 161B of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B, while retraction of the piston heads 134A, 134B away from the cassette 112 can increase the volume of the pump chambers 138A, 138B and cause dialysate to be drawn into the pump chambers 138A, 138B.

As shown in FIG. 3, the cassette interface 110 includes two pressure sensors 151A, 151B that align with pressure sensing chambers 163A, 163B (shown in FIG. 2) of the cassette 112 when the cassette 112 is positioned within the cassette compartment 114. Portions of a membrane 140 of the cassette 112 that overlie the pressure sensing chambers 163A, 163B adhere to the pressure sensors 151A, 151B using vacuum pressure. Specifically, clearance around the pressure sensors 151A, 151B communicates vacuum to the portions of the cassette membrane 140 overlying the pressure sensing chambers 163A, 163B to hold those portions of the cassette membrane 140 tightly against the pressure sensors 151A, 151B. The pressure of fluid within the pressure sensing chambers 163A, 163B causes the portions of the cassette membrane 140 overlying the pressure sensing chambers 163A, 163B to contact and apply pressure to the pressure sensors 151A, 151B.

The pressure sensors 151A, 151B can be any sensors that are capable of sensing the fluid pressure in the sensing chambers 163A, 163B. In some implementations, the pressure sensors are solid state silicon diaphragm infusion pump force/pressure transducers. One example of such a sensor is the Model 1865 force/pressure transducer manufactured by Sensym Foxboro ICT. In certain implementations, the force/pressure transducer is modified to provide increased voltage output. The force/pressure transducer can, for example, be modified to produce an output signal of 0 to 5 volts.

Still referring to FIG. 3, the PD cycler 102 also includes multiple inflatable members 142 positioned within inflatable member ports 144 in the cassette interface 110. The inflatable members 142 align with depressible dome regions (not shown) of the cassette 112 when the cassette 112 is positioned within the cassette compartment 114 of the PD cycler 102. Dialysate can be pumped through the cassette 112 by actuating the piston heads 134A, 134B, and can be guided along desired flow paths within the cassette 112 by selectively inflating and deflating the various inflatable members 142.

Still referring to FIG. 3, locating pins 148 extend from the cassette interface 110 of the PD cycler 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD cycler 102, as shown in FIG. 3, defines cylindrical recesses 152A, 152B that substantially align with the pistons 133A, 133B when the door 108 is in the closed position. When the cassette 112 is positioned within the cassette compartment 114, hollow projections 154A, 154B of the cassette 112, inner surfaces of which partially define the pump chambers 138A, 138B, fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the projections 154A, 154B of the cassette 112 and the planar surface of the door 108 supports the other regions of the cassette 112. The door 108 can counteract the forces applied by the inflatable members 142 and thus allows the inflatable members 142 to actuate the depressible dome regions 146 on the cassette 112. The engagement between the door 108 and the hollow projections 154A, 154B of the cassette 112 can also help to hold the cassette 112 in a desired fixed position within the cassette compartment 114 to further ensure that the pistons 133A, 133B align with the fluid pump chambers 138A, 138B of the cassette 112.

A control unit 139 (shown in FIG. 1), e.g., a microprocessor, is connected to the pressure sensors 151A, 151B, to the stepper motors (e.g., the drivers of the stepper motors) that drive the pistons 133A, 133B, and to the encoders that monitor rotation of the lead screws of the stepper motors such that the control unit 139 can receive signals from and transmit signals to those components of the system. In some implementations, the control unit 139 is an MPC823 PowerPC device manufactured by Motorola, Inc.

The control unit 139 monitors the components to which it is connected to determine whether any complications exists within the PD system 100. In the event of complications, the control unit 139 triggers one or more alarms which warn a patient or operator of the PD system 100 of conditions, e.g., conditions requiring attention from the patient or operator. The alarms can include audio alerts (e.g, generated by a speaker), visual alerts (e.g., displayed on touch screen 118), or other kinds of alerts.

One such condition for triggering an alarm is a state of the heater tray 116 and heater bag 124. For example, if the heater tray 116 or heater bag 124 requires attention from a patient or operator, an alarm may be triggered. The heater tray 116 or heater bag 124 requires attention if the heater bag 124 is positioned incorrectly on the heater tray 116. The heater tray 116 or heater bag 124 also requires attention if the heater bag 124 is absent from the heater tray 116. In some implementations, the control unit 139 can determine if the heater 124 bag is positioned incorrectly or absent based on measurements obtained using one or more temperature sensors such as thermistors.

Figure 4A:
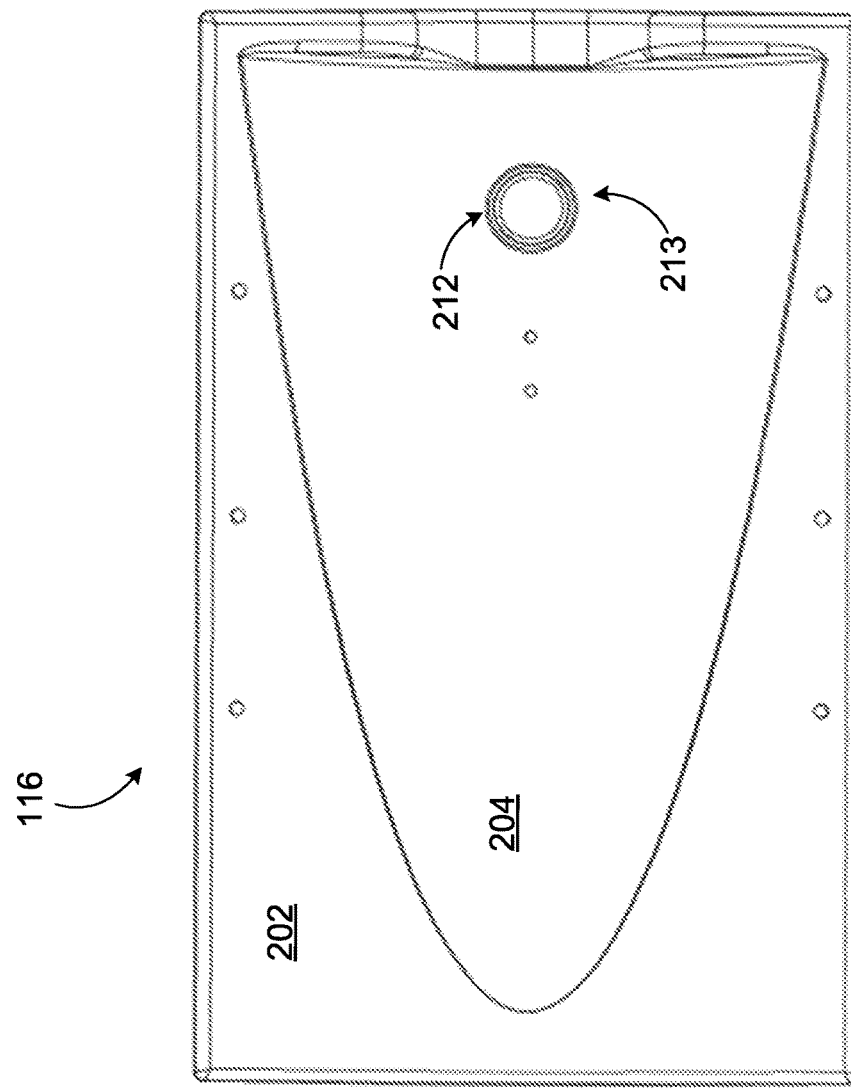
Figure 4C:
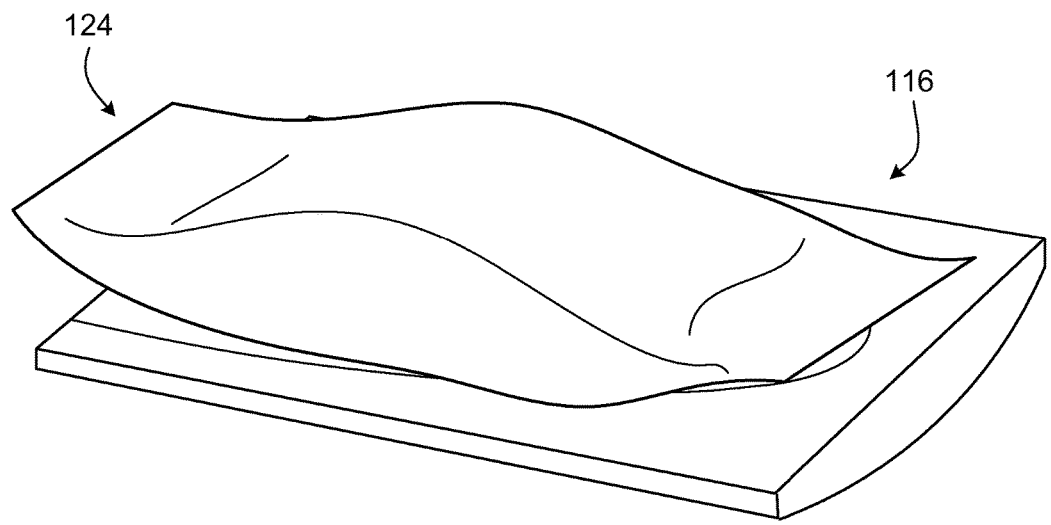
Figure 4D:
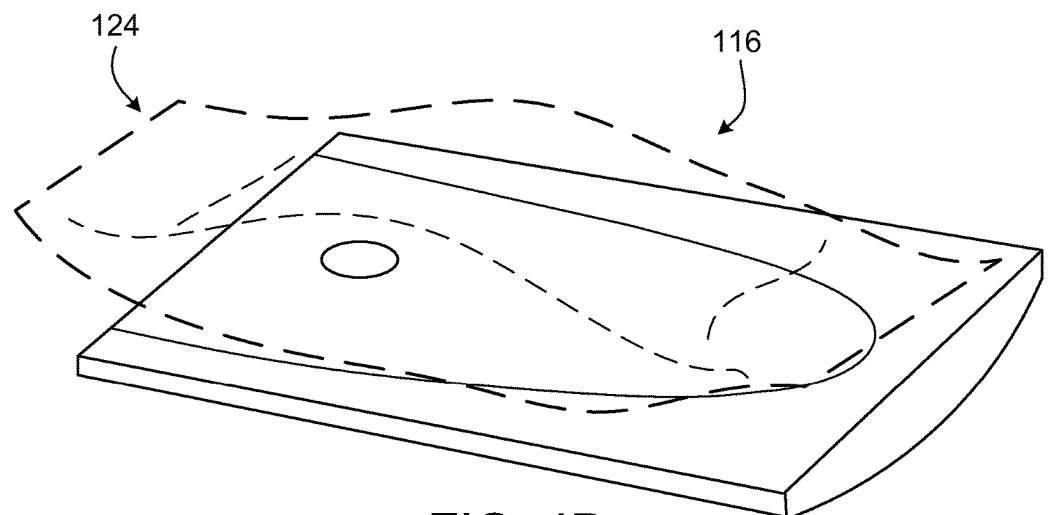
Figure 4E:
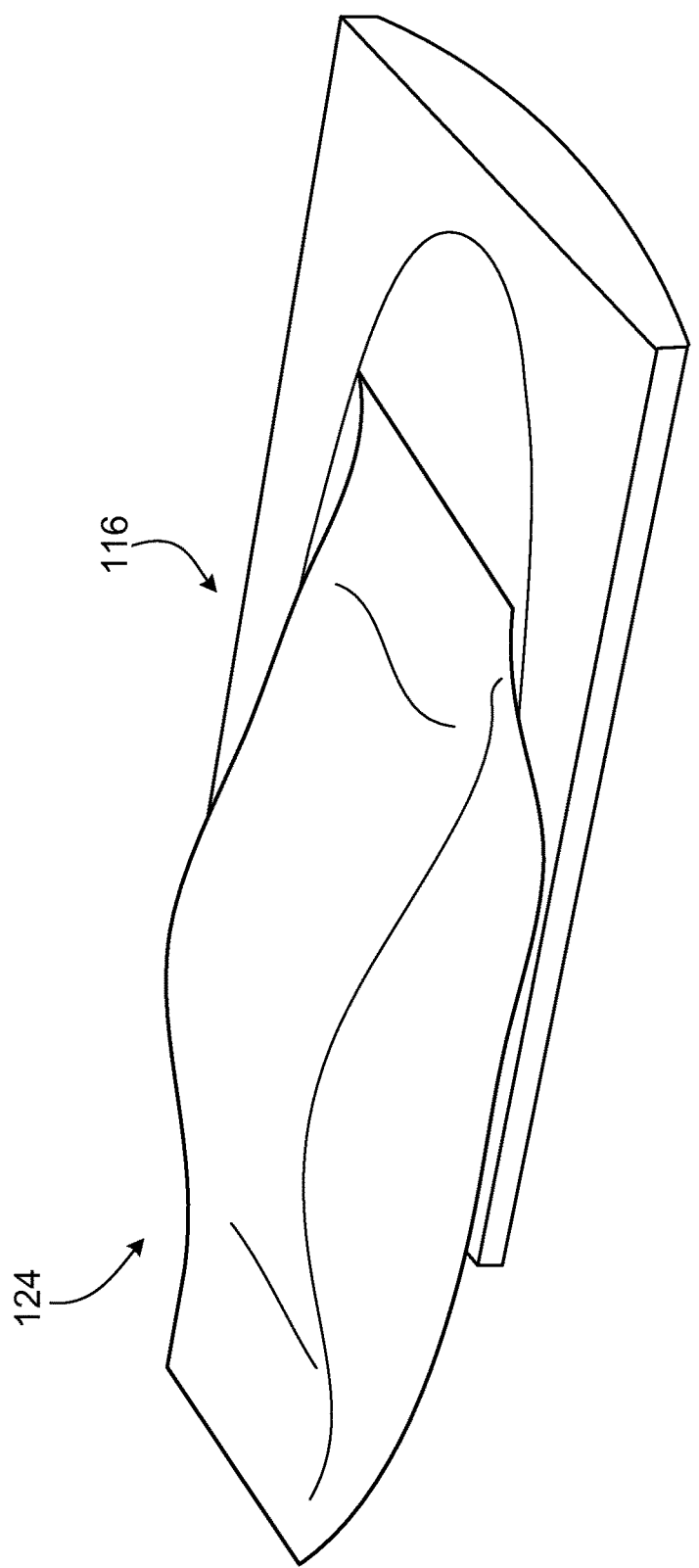

FIGS. 4A-4E show the heater tray 116 in detail. Referring to FIG. 4A, a top surface 202 of the heater tray 116 defines a shallow concave indentation 204. The indentation 204 is sized and shaped to receive the heater bag 124 (FIG. 1). When the heater bag 124 is placed at the indentation 204, the heater bag 124 is cradled by the indentation in a manner that increases the contact between the heater bag 124 and the top surface 202. In particular, the heater bag 124 comprises a pliable material that conforms to the shape of solid objects in contact with the heater bag 124. Thus, when the heater bag 124 is placed on top surface 202 at the indentation 204 the heater bag 124 will conform to the shape of the indentation 204.

Referring to FIG. 4B, a bottom surface 206 of the heater tray 116 is in contact with a surface of a heating element 208. The heating element 208 generates heat when electricity is applied to it. For example, electricity could be applied to the heating element 208 based on a control output from the control unit 139. When the heating element 208 generates heat, the heat is conducted by the body 210 of the heater tray 116. When heat is conducted by the body 210 of the heater tray 116, the indentation 204 will warm up and conduct heat to the heater bag 124.

The heater tray 116 includes at least one sensing element 212. The sensing element 212 is used to measure a value indicative of the state of the heater tray 116 and heater bag 124. In some implementations, the sensing element 212 measures temperature, such that the value indicative of the state of the heater tray 116 and heater bag 124 is the temperature of the heater tray 116. The temperature of the heater tray 116 can be used, in particular, to measure temperature changes that would indicate that the heater bag 124 is positioned incorrectly or absent.

An example of an element that measures temperature is a thermistor, which is a resistor having a resistance that varies with temperature in a manner that can be measured, e.g., when current flows through the thermistor. Thus, the voltage drop across the thermistor will vary according to temperature, and can be measured to determine a current temperature of the thermistor. While resistors other than thermistors sometimes have a resistance that varies with temperature, a thermistor tends to have a resistance that changes with temperature more significantly and/or more consistently than other types of resistors. In some implementations, the sensing element 212 could include one or more (e.g., two) thermistors.

A rate of change in temperature measured by the sensing element 212 can be used to infer whether the heater bag 124 is positioned incorrectly or absent. For example, referring to FIG. 4C, when the heater bag 124 is positioned correctly on the heater tray 116, the heater bag 124 will absorb heat from the top surface 202 of the heater tray 116 (e.g., by conducting heat from the top surface 202). The heater bag 124 is positioned such that most of one surface of the heater bag is in contact with the heater tray 116. In general, a heater bag is correctly positioned on the heater tray if a threshold amount of heater bag surface (e.g., 40% of the total surface) is in physical contact with the heater tray.

The temperature measured by the sensing element 212 will be affected by the presence of the heater bag 124. For example, if the heater bag 124 is present while the heater tray 116 is warming up, the rate at which the heater tray 116 warms up will be affected by the heat absorption of the heater bag 124. In contrast, referring to FIG. 4D, when the heater bag 124 is absent from the heater tray 116, heat will not be absorbed from the top surface 202 of the heater tray. Thus, the heater tray 116 will warm up more quickly than if the heater bag 124 were present. Further, referring to FIG. 4E, if the heater bag 124 is positioned incorrectly on the heater tray 116 (e.g., less than a threshold amount of the heater bag surface is in contact with the heater tray), heat will be absorbed from the top surface 202 of the heater tray, but at a slower rate than if the heater bag 124 were positioned correctly on the heater tray 116.

The control unit 139 (FIG. 1) is in communication with the sensing element 212 and calculates temperature data based on signals received from the sensing element 212. The control unit 139 can determine, over a period of time, whether the temperature data indicates the heater bag 124 is positioned correctly on the heater tray 116, or positioned incorrectly on the heater tray 116, or absent from the heater tray 116.

In some implementations, multiple sensing elements 212 are used. For example, as shown in FIGS. 4A-4B, a second sensing element 214 can be included in the heater tray 116. In some implementations, the second sensing element 214 is positioned at a different location 215 than the location 213 of the first sensing element 212. In this way, the second sensing element 213 can measure temperature change at a different location than temperature change at the location of the first sensing element.

In some implementations, one of the sensing elements is positioned in a manner such that the sensing element 212 contacts the heater bag 124 when the heater bag 124 is positioned correctly on the heater tray 116. The other sensing element can be positioned in a manner such that the other sensing element 214 is positioned near or contacts the heating element 208. In this way, the measurements of the first sensing element 212 tend to be affected more greatly depending on the position of the heater bag 124. In contrast, the measurements of the second sensing element 214 tend to be affected more greatly depending on the presence or absence of the heater bag 124, e.g., depending on how much heat generated by the heating element 208 is absorbed, e.g., as the heating element 208 heats up.

In some implementations, the control unit 139 can make this determination based on a look-up table of stored data. The look-up table can correspond to excepted values for temperate under a certain scenario, such as the scenario in which a heater bag is placed on the heater tray at room temperature and then the heating element is engaged to begin heating the tray. For example, the look-up table can include expected values for the measured temperature at points in time, e.g., after one second, five seconds, ten seconds, etc. If the actual temperature measured based on the signals from the sensing element 212 is similar to the temperature values of the look-up table, the control unit 139 can infer that the heater bag is correctly positioned on the heater tray. When we say that the actual measured temperature is similar to the stored expected temperature values of the look-up table, we mean that the actual measured temperature meets an upper and lower bound of values relative to the stored expected value at points in time.

For example, the upper bound may be five degrees (e.g., Fahrenheit) above the stored expected value, and the lower bound may be five degrees below the stored expected value. Thus, if the actual measured temperature is within five degrees or less than the stored expected value, then the actual measured temperature can be said to be similar to the stored expected value.

Further, a threshold number of similar values could be used by the control unit 129 to determine if the actual measured temperature values indicate that the heater bag is correctly positioned on the heater tray. For example, if the look-up table has ten values (e.g., expected values for every ten seconds over a period of one hundred seconds), a threshold of eight may be used. (This is only an example, and in practice the look-up table could have a number of values other than ten, e.g., dozens or hundreds or more.) Thus, if the control unit 139 determines that at least eight of the ten actual measured temperature values are similar to the corresponding eight value of the look-up table for the same time indicies, then the control unit 139 can infer that the heater bag is correctly positioned on the heater tray. In contrast, if fewer than eight of the ten actual measured temperature values are similar to the values of the look-up table for the same time indicies, then the control unit 139 can infer that the heater bag is not correctly positioned on the heater tray, even if some of the temperature values are in fact similar to stored values for the same time indices.

An example of a look-up table is shown in Table 1. This example of a look-up table includes minimum and maximum values for temperature at multiple time indices. One pair of columns represents values of minimum and maximum temperature for a heater bag (e.g., the heater bag 124 shown in FIG. 1) and another of columns represents values of minimum and maximum temperature for a heater tray (e.g., the heater tray 116 shown in FIG. 1).

TABLE 1

| Time (s) | Bag Minimum (° C.) | Bag Maximum (° C.) | Tray Minimum (° C.) | Tray Maximum (° C.) |
| --- | --- | --- | --- | --- |
| 5 | 25 | 30 | 35 | 40 |
| 10 | 30 | 35 | 40 | 45 |
| 15 | 35 | 40 | 45 | 50 |
| 20 | 40 | 45 | 50 | 55 |
| 25 | 45 | 50 | 55 | 60 |

In this example, in use, the control unit 139 can consult the look-up table and compare measured values to the values of the look-up table. For example, the control unit 139 may compare values measured at a sensing element (e.g., the first sensing element 212 shown in FIGS. 4A and 4B) at a particular time index (e.g., 5 seconds) to the values of the look-up table for the "Bag Minimum" and "Bag Maximum" columns. If the measured value at the sensing element is 27 degrees Celsius then the control unit 139 can record data indicating that the value measured at that time index was within an expected range specified by the look-up table. In contrast, if the measured value at the sensing element is 40 degrees Celsius then the control unit 139 can record data indicating that the value measured at that time index was not within the expected range specified by the look-up table. The control unit 139 can make this comparison for multiple time indices represented by the look-up table to determine if the measured data suggests that the heater bag is present and/or properly positioned on the heater tray.

In some implementations, multiple look-up tables could be used. For example, one look-up table may represent expected values for a heater bag status of "present and properly positioned," another look-up table may represent expected values for a heater bag status of "improperly positioned," and another look-up table may represent expected values for a heater bag status of "absent." The control unit 139 can compare measured values to each of the look-up tables to determine which, if any, corresponds most closely to the measured values.

In some implementations, a single look-up table could be used. For example, a look-up table could be used that represents expected values of temperature readings (e.g., from one or more temperature sensors) when a heater bag is correctly positioned on a heater tray. The control unit 139 can use a stored algorithm (e.g., as part of program code executed by the control unit 139) to interpret the comparison between the look-up table and data received by the control unit 139 representing measured temperature values. For example, the stored algorithm can indicate that if the measured values are different from the look-up table values by X degrees for Y time period, then the heater bag is likely positioned incorrectly, and/or that if the measured values are different from the look-up table values by A degrees for B time period then the heater bag is likely absent from the heater tray.

Figure 5A:
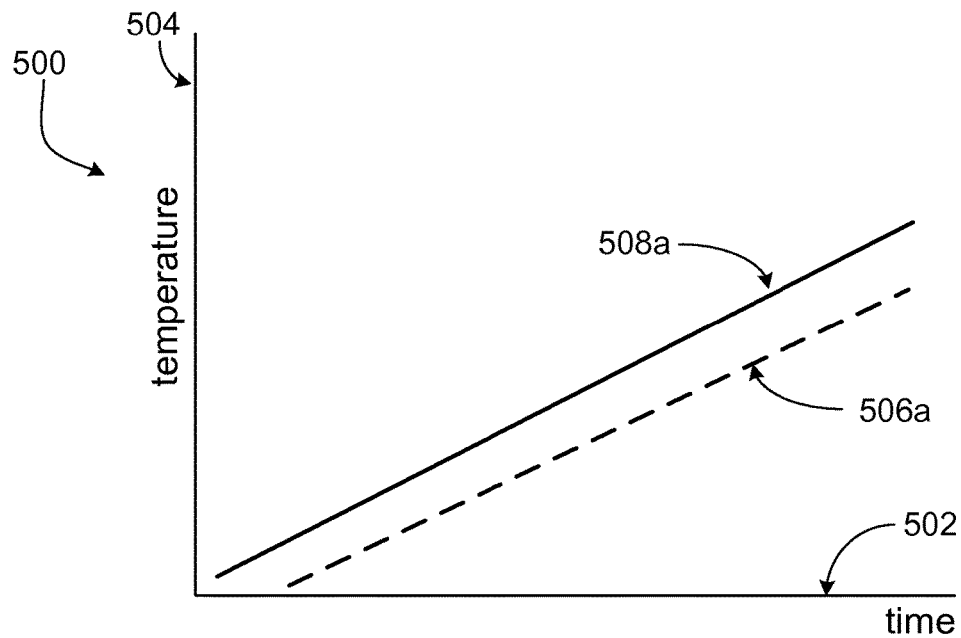
FIGS. 5A-5C are graphs of temperature data.
Figure 5B:
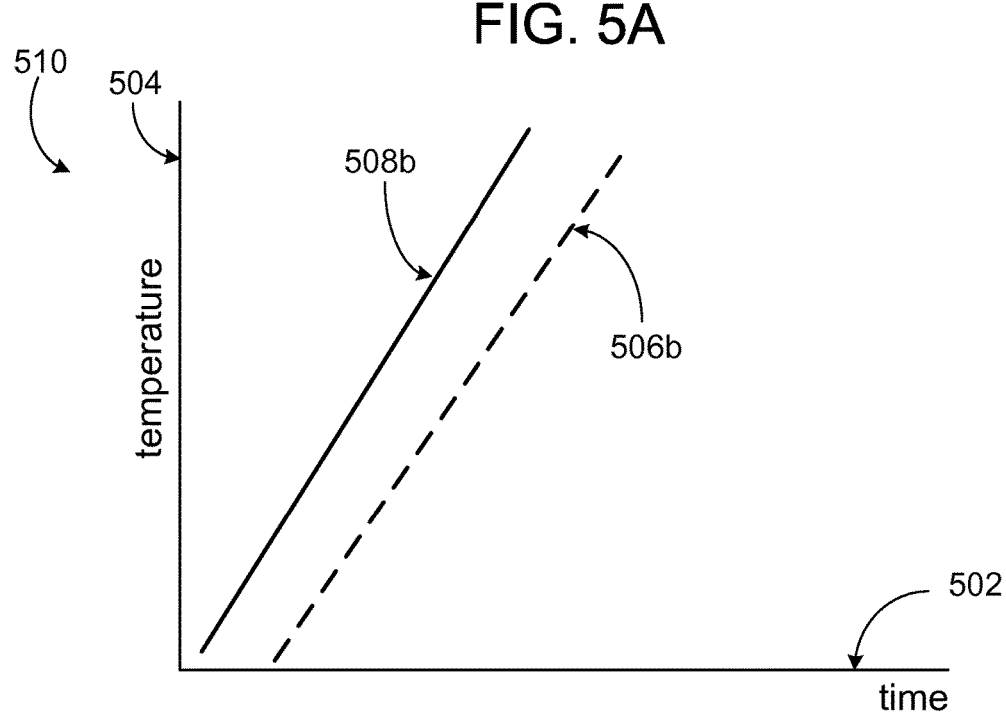
Figure 5C:
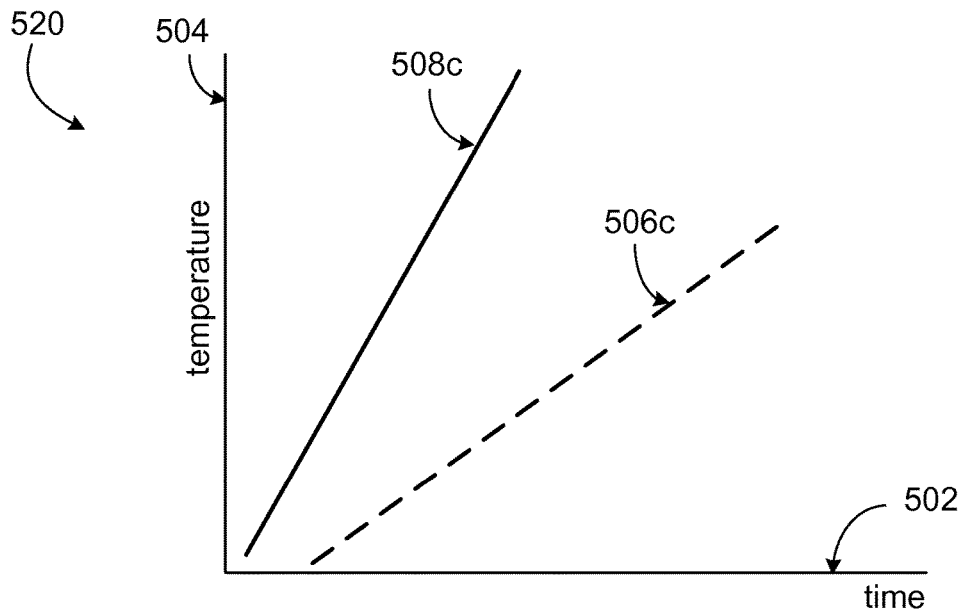

FIGS. 5A, 5B, and 5C each show respective graphs 500, 510, 520 of temperature values measured at multiple sensing elements. For example, the graphs 500, 510, 520 could represent temperature values measured at the sensing elements 212, 214 shown in FIGS. 4A-4B. Each graph 500, 510 has an x-axis 502 representing time (in seconds) and a y-axis 504 representing temperature (in degrees Celsius). Each graph 500, 510 includes respective lines 506*a*, 506*b*, 506*c* (shown as dotted lines) representing the temperature, over time, at the first sensing element and respective lines 508*a*, 508*b*, 508*c* (shown as solid lines) representing the temperature, over time, at the second sensing element. For example, the first sensing element can be the first sensing element 212 shown in FIGS. 4A-4B and the second sensing element can be the second sensing element 214 shown in FIGS. 4A-4B.

As shown in the first graph 500, the first line 506a and the second line 508a are characterized by approximately the same slope. This graph 500 represents a situation in which the heater bag is correctly placed on the heater tray. Because the first line 506a and the second line 508a are characterized by approximately the same slope, the data underlying the graph 500 indicates that the two sensing elements from which the data are derived are measuring similar rates of change in temperature. If one sensing element is sensing the temperature of a heater tray, and another sensing element is sensing the temperature of a heating element, then heat is being absorbed from the heater tray and the heating element at approximately the same rate.

When we say "approximately the same slope," the slopes need not be the same slope, but could be within a threshold difference. For example, the threshold could be 0.5 degrees/sec, and the slope of one line could be 1.8 degrees/sec, and the slope of the other line could be 2.1 degrees/sec. Because the slopes are within 0.5 degrees/sec, the lines have approximately the same slope.

In addition, the control unit 139 can compare the slopes of the lines to stored data, e.g., a stored profile such as the look-up table shown in Table 1. If the data underlying the graph 500 corresponds to values of a stored look-up table (e.g., using the data point comparison technique described above), then the comparison can be used to determine a status of the heater bag. For example, a look-up table corresponding to the rate of heat absorption characterized by this graph 500 may be associated with a heater bag status of "properly positioned." Thus, the control unit 139 can use this data, including the slopes of the lines, to determine that the heater bag is properly positioned on the heater tray.

As shown in the second graph 510, the first line 506b and the second line 508b are characterized by approximately the same slope. This graph 500 represents a situation in which the heater bag is absent from the heater tray. Here, the slopes of the lines 506b, 508b are greater than the slopes of the lines 506a, 508a of the first graph 500. Thus, the corresponding temperature sensors are sensing that the heater tray and the heating element are both heating up quickly, and thus heat is not being absorbed from the heater tray. In this way, the control unit 139 can use this data to determine that the heater bag is absent from the heater tray, e.g., by comparing the data of this graph 510 to data of a look-up table.

As shown in the third graph 520, the first line 506c and the second line 508c are characterized by different slopes. This graph 500 represents a situation in which the heater bag is present on the heater tray, but incorrectly positioned. Here, the slope of the line 506c representing the temperature values of the first sensing element is less than the slope of the line representing the temperature values of the second sensing element. Thus, heat is being absorbed at the site of the first sensing element (positioned at the heater tray), but heat is not being absorbed as expected at the second sensing element (positioned at the heating element). Thus, although a heater bag may be present and absorbing heat from the heater ray, the heater bag is not positioned in a way that it is absorbing sufficient heat from the heating element. In this way, the control unit 139 can use this data to determine that the heater bag is positioned incorrectly on the heater tray, e.g., by comparing the data of this graph 510 to data of a look-up table.

The graphs 500, 510, 520 are only examples and many other scenarios are possible. Other types of graphs, e.g., having different slopes or patterns of data, may indicate other types of scenarios. For example, there may be a scenario in which heat is being absorbed from the heating element and heating tray (e.g., such that the data of the two sensing elements has approximately the same slope), but not at the rate characteristic of a correctly positioned heater bag. However the data from the sensing elements may indicate that some heat is still being absorbed, indicating that a heater bag is present and correctly positioned. In this scenario, a heater bag may be present, but may contain an amount of dialysate less than a threshold, e.g., a threshold indicating a sufficient amount of dialysate used in a PD treatment. The control unit 139 can use the technique of evaluating slopes and or comparing with data of look-up tables to determine that a heater bag contains an insufficient amount of dialysate.

Figure 6:
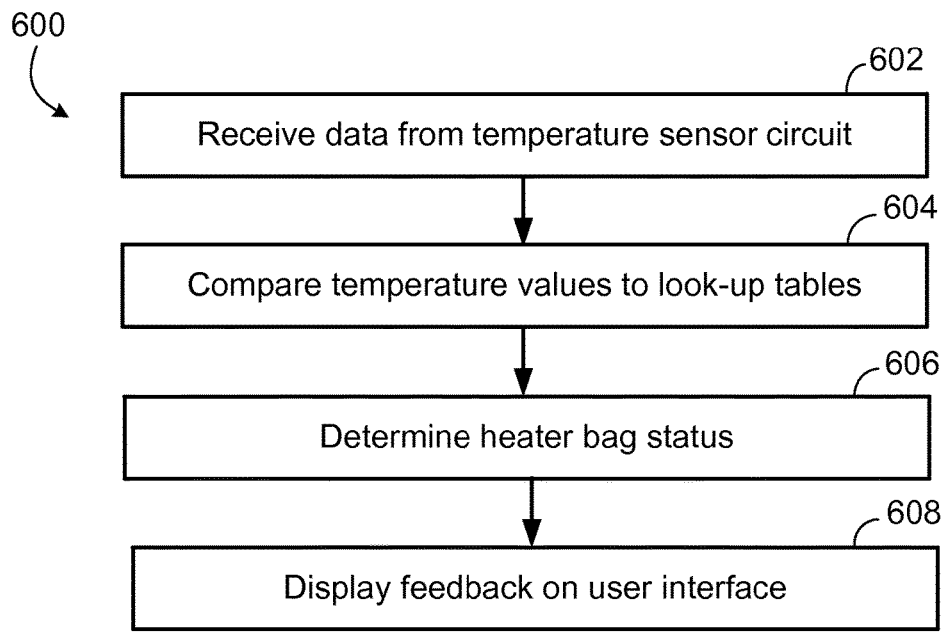
FIG. 6 is a flowchart of a process for determining a status of a heater bag.

FIG. 6 shows a procedure 600 that could be used to determine if a heater bag is correctly positioned on a heater tray (e.g., the heater bag 124 and heater tray 106 shown in FIG. 1). For example, the procedure 600 could be carried out by the control unit 139 of the PD system 100 shown in FIG. 1.

Data is received (602) from a temperature sensor circuit. For example, the temperature sensor circuit could include one or more temperature sensors such as thermistors. In some examples, multiple temperature sensors and/or multiple temperature sensor circuits are used. In some implementations, the temperature sensor circuit includes a temperature sensor and one or more components that interface with a microcontroller or microprocessor (e.g., a microcontroller or microprocessor such as the control unit 139) such as an analog-to-digital converter (ADC). In some implementations, readings from the temperature sensor circuit may be analog readings (such as voltage levels) and are converted to digital data by one or more components of a microcontroller, e.g., a microcontroller having built-in analog-to-digital conversion functionality. In some implementations a temperature sensor outputs digital data, e.g., has a built-in analog-to-digital converter, such that the temperature sensor can communicate digital data to a digital input of a microprocessor or microcontroller.

Temperature values are compared (604) to one or more look-up tables. The temperature values are determined based on the data received from the temperature sensor circuit. For example, the look-up tables can be stored in data storage and retrieved by the control unit 139.

The heater bag status is determined (606) based on the comparison of the temperature values. In some examples, if the temperature values match one of the look-up tables (within a certain threshold or tolerance), then the heater bag status can be determined based on the identification of this match. The heater bag status is a status other than a temperature of the heater bag, e.g., a status such as whether the heater bag is positioned on the heater tray, and/or whether the positioning of the heater bag is correct with respect to design parameters for heat absorption. For example, if the look-up table is associated with a heater bag status of "absent," and the temperature values match the look-up table, then the heater bag status can be determined to be "absent."

Feedback is displayed (608) on a user interface. For example, the user interface can be a module of the PD machine 100 shown in FIG. 1. In some examples, the user interface is generated by software and displayed by one or more hardware components. In some implementations, the user interface is displayed on a display device 118 (e.g., a touch screen) of the PD machine 100 (FIG. 1). The feedback can include one or more messages related to the status of the heater bag. For example, messages can include one or more images or text communicating concepts such as "heater bag is not present on heater tray; please place heater bag on tray" or "heater bag is not positioned correctly on heater tray; please position heater bag correctly." The message could include text messages as well as images representing these concepts, e.g., an image showing correct positioning of the heater bag.

Figure 7:
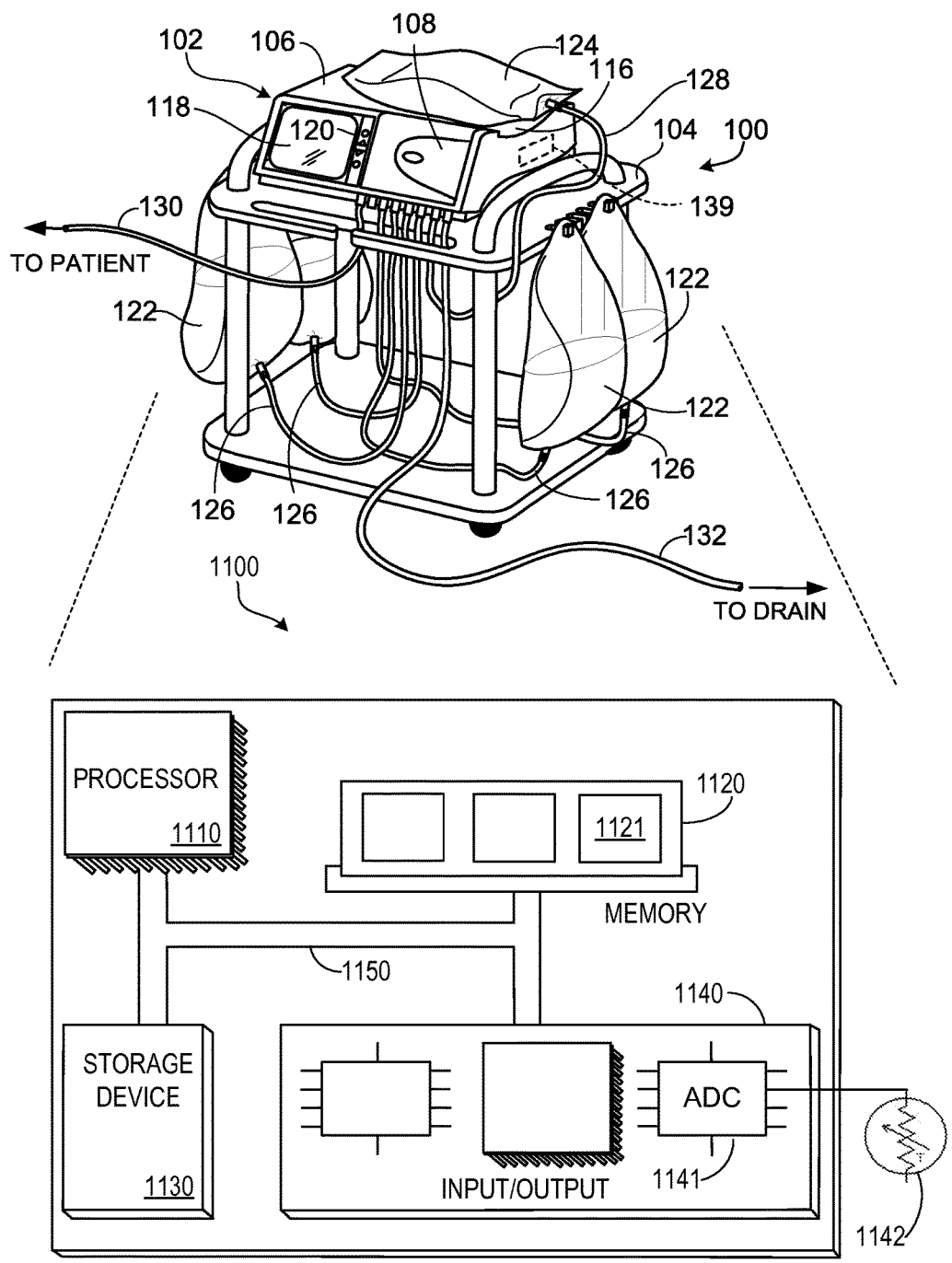
FIG. 7 is an example computer system.
Like reference symbols in the various drawings indicate like elements.

FIG. 7 is a block diagram of an example computer system 1100. For example, referring to FIG. 1, the control unit 139 could be an example of the system 1100 described here. The system 1100 includes a processor 1110, a memory 1120, a storage device 1130, and an input/output interface 1140. Each of the components 1110, 1120, 1130, and 1140 can be interconnected, for example, using a system bus 1150. The processor 1110 is capable of processing instructions for execution within the system 1100. The processor 1110 can be a single-threaded processor, a multi-threaded processor, or a quantum computer. The processor 1110 is capable of processing instructions stored in the memory 1120 or on the storage device 1130. The processor 1110 may execute operations such as receiving signals from a sensing element (e.g., the sensing element 212 shown in FIGS. 4A-4B) and comparing data based on the signals to stored data, e.g., data stored in a look-up table of temperature values.

The memory 1120 stores information within the system 1100. In some implementations, the memory 1120 is a computer-readable medium. The memory 1120 can, for example, be a volatile memory unit or a non-volatile memory unit. In some implementations, the memory 1120 stores a look-up table 1121, e.g., the look-up table described above with respect to Table 1. In some implementations, multiple look-up tables 1121 are used.

The storage device 1130 is capable of providing mass storage for the system 1100. In some implementations, the storage device 1130 is a non-transitory computer-readable medium. The storage device 1130 can include, for example, a hard disk device, an optical disk device, a solid-date drive, a flash drive, magnetic tape, or some other large capacity storage device. The storage device 1130 may alternatively be a cloud storage device, e.g., a logical storage device including multiple physical storage devices distributed on a network and accessed using a network.

The input/output interface 1140 provides input/output operations for the system 1100. In some implementations, the input/output interface 1140 includes one or more of network interface devices (e.g., an Ethernet card), a serial communication device (e.g., an RS-232 10 port), and/or a wireless interface device (e.g., an 802.11 card, a 3G wireless modem, or a 4G wireless modem). In some implementations, the input/output device includes driver devices configured to receive input data and send output data to other input/output devices, e.g., keyboard, printer and display devices 118. In some implementations, mobile computing devices, mobile communication devices, and other devices are used.

In some implementations, the input/output interface 1140 includes at least one analog-to-digital converter 1141. An analog-to-digital converter converts analog signals to digital signals, e.g., digital signals suitable for processing by the processor 1100. In some implementations, one or more sensing elements (e.g., the sensing elements 212, 214 shown in FIGS. 4A-4B) are in communication with the analog-to-digital converter 1141. For example, if a sensing element includes at least one thermistor 1142, the thermistor 1142 can be placed in an electrical circuit with the analog-to-digital converter 1141. In some implementations, the thermistor 1142 is directly connected to the analog-to-digital converter 1141, e.g., connected such that no other components are placed between the thermistor 1142 and the analog-to-digital converter 1141 in the electrical circuit. In some implementations, the thermistor 1142 is not directly connected to the analog-to-digital converter 1141. For example, the circuit containing the thermistor 1142 and the analog-to-digital converter 1141 could contain other components such as an operational amplifier and/or a buffer circuit. In some implementations, a differential amplifier circuit is placed in series between the thermistor 1142 and an input lead of the analog-to-digital converter 1141.

In some implementations, the system 1100 is a microcontroller. A microcontroller is a device that contains multiple elements of a computer system in a single electronics package. For example, the single electronics package could contain the processor 1110, the memory 1120, the storage device 1130, and input/output interfaces 1140.

Although an example processing system has been described in FIG. 7, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. Accordingly, other embodiments are within the scope of the following claims.

What is claimed is:

1. A peritoneal dialysis machine, comprising
a source of dialysate;
a patient line for passing dialysate to and from the patient's abdominal cavity;
a controller for delivering a quantity of dialysate to the patient's abdomen via the patient line;
a heater tray for heating a heater bag containing the dialysate before delivering it to the patient, the heater tray comprising a temperature sensor; and
at least one processor configured to receive input data from the temperature sensor and determine, based on input data received from the temperature sensor over a period of time, a status of the heater bag other than a temperature of the heater bag,
wherein the temperature sensor comprises a first thermistor and a second thermistor, wherein the processor is configured to determine whether the heater bag is positioned on the heater tray based on output of the first thermistor, and the processor is configured to determine whether the heater bag positioned on the heater tray is correctly positioned based on output of the second thermistor.

2. The peritoneal dialysis machine of claim 1 wherein the status of the heater bag comprises presence of the heater bag on the heater tray.

3. The peritoneal dialysis machine of claim 1 wherein the status of the heater bag comprises correct positioning of the heater bag on the heater tray.

4. The peritoneal dialysis machine of claim 1 wherein the heater tray comprises a heating element, and the temperature sensor is configured to measure a temperature of the heating element.

5. The peritoneal dialysis machine of claim 1, comprising data storage, wherein the processor is configured to compare the input data received from the temperature sensor over a period of time to data stored in the data storage, the data representing a stored profile of expected input data.

6. The peritoneal dialysis machine of claim 5, wherein
the input data comprises temperature values generated at respective time indices;
the stored profile comprises reference temperature values corresponding to at least some of the respective time indices;
determining whether the heater bag is positioned on the heater tray comprises determining, for a threshold number of the time indices, whether the temperature values of the input data are within a threshold percentage range compared to the reference temperature values of the stored profile.

7. A peritoneal dialysis machine, comprising
a source of dialysate;
a patient line for passing dialysate to and from the patient's abdominal cavity;
a controller for delivering a quantity of dialysate to the patient's abdomen via the patient line;
a heater tray for heating a heater bag containing the dialysate before delivering it to the patient, the heater tray comprising a temperature sensor;
at least one processor configured to receive input data from the temperature sensor and determine, based on input data received from the temperature sensor over a period of time, a status of the heater bag other than a temperature of the heater bag; and
data storage, wherein the processor is configured to compare the input data received from the temperature sensor over a period of time to data stored in the data storage, the data representing a stored profile of expected input data,
wherein the input data comprises temperature values generated at respective time indices,
wherein the stored profile comprises reference temperature values corresponding to at least some of the respective time indices, and
wherein determining whether the heater bag is positioned on the heater tray comprises determining, for a threshold number of the time indices, whether the temperature values of the input data are within a threshold percentage range compared to the reference temperature values of the stored profile.

8. The peritoneal dialysis machine of claim 7, wherein the temperature sensor comprises a first thermistor and a second thermistor, wherein the processor is configured to determine whether the heater bag is positioned on the heater tray based on output of the first thermistor, and the processor is configured to determine whether the heater bag positioned on the heater tray is correctly positioned based on output of the second thermistor.

9. The peritoneal dialysis machine of claim 7 wherein the status of the heater bag comprises presence of the heater bag on the heater tray.

10. The peritoneal dialysis machine of claim 7 wherein the status of the heater bag comprises correct positioning of the heater bag on the heater tray.

11. The peritoneal dialysis machine of claim 7 wherein the heater tray comprises a heating element, and the temperature sensor is configured to measure a temperature of the heating element.

12. A peritoneal dialysis system, comprising:
a peritoneal dialysis machine for delivering a quantity of dialysate to a patient's abdomen;
a heater tray for heating a heater bag containing dialysate before delivering it to the patient via the peritoneal dialysis machine, the heater tray comprising a temperature sensor; and
at least one processor configured to receive input data from the temperature sensor and determine, based on input data received from the temperature sensor over a period of time, a status of the heater bag other than a temperature of the heater bag,
wherein the temperature sensor comprises a first thermistor and a second thermistor, wherein the processor is configured to determine whether the heater bag is positioned on the heater tray based on output of the first thermistor, and the processor is configured to determine whether the heater bag positioned on the heater tray is correctly positioned based on output of the second thermistor.

13. The peritoneal dialysis system of claim 12 wherein the status of the heater bag comprises presence of the heater bag on the heater tray.

14. The peritoneal dialysis system of claim 12 wherein the status of the heater bag comprises correct positioning of the heater bag on the heater tray.

15. The peritoneal dialysis system of claim 12 wherein the heater tray comprises a heating element, and the temperature sensor is configured to measure a temperature of the heating element.

16. The peritoneal dialysis system of claim 12, comprising data storage, wherein the processor is configured to compare the input data received from the temperature sensor over a period of time to data stored in the data storage, the data representing a stored profile of expected input data.

17. The peritoneal dialysis system of claim 16, wherein
the input data comprises temperature values generated at respective time indices;
the stored profile comprises reference temperature values corresponding to at least some of the respective time indices;
determining whether the heater bag is positioned on the heater tray comprises determining, for a threshold number of the time indices, whether the temperature values of the input data are within a threshold percentage range compared to the reference temperature values of the stored profile.

* * * * *